United States Patent [19]

Latimer et al.

[11] Patent Number: 5,035,143
[45] Date of Patent: Jul. 30, 1991

[54] METHOD OF DETECTING CREEP SWELLING

[75] Inventors: Paul J. Latimer; Hubert L. Whaley, both of Lynchburg, Va.

[73] Assignee: The Babcock & Wilcox Company, New Orleans, La.

[21] Appl. No.: 507,427

[22] Filed: Apr. 10, 1990

[51] Int. Cl.$^5$ ............................................. G01N 29/00
[52] U.S. Cl. ........................................ 73/598; 73/622; 73/597; 364/502; 367/127
[58] Field of Search ................. 73/597, 622, 627, 598, 73/730; 364/502; 367/127; 33/1 P

[56] References Cited

U.S. PATENT DOCUMENTS

| | | | |
|---|---|---|---|
| 4,049,954 | 9/1977 | Da Costa Viera et al. | 73/627 |
| 4,420,980 | 12/1983 | Dunemann et al. | 73/730 |
| 4,567,747 | 2/1986 | Matay | 73/622 |

FOREIGN PATENT DOCUMENTS 54-99665  8/1979  Japan ..................................... 73/622

OTHER PUBLICATIONS

"An Integrated Circuit Pulse Echo Overlap Facility for Measurement of Velocity of Sound" by A. G. Hellier, S. B. Palmer, and D. G. Whitehead, (Journal of Physics E, vol. 8, No. 5, pp. 352-354, May 1975).

Primary Examiner—Hezron E. Williams
Assistant Examiner—Rose M. Finley
Attorney, Agent, or Firm—Vytas R. Matas; Robert J. Edwards; Daniel S. Kalka

[57] ABSTRACT

A method is disclosed for ultrasonically detecting creep swelling in tubular members such as fossil utility steam lines and headers. Ultrasonic surface waves (34) are propagated around the pipe (10) in a circumferential direction. The transit time ($\Delta T$) is measured by using the pulse overlap technique with an oscilloscope (24). Circumferential dimension is obtained by multiplying the transit time ($\Delta T$) by the known Raleigh velocity of sound in the tubular member.

6 Claims, 1 Drawing Sheet

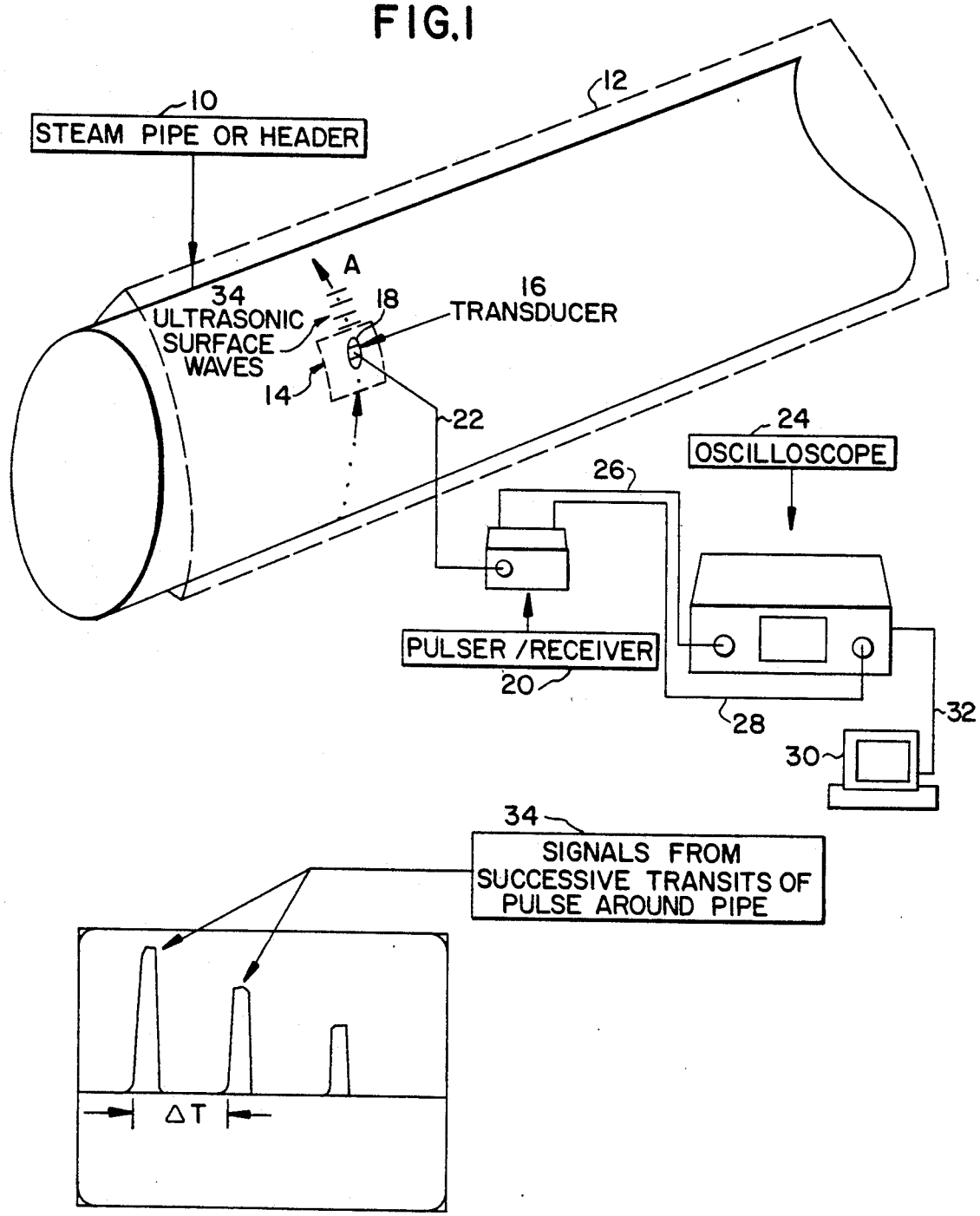

METHOD OF DETECTING CREEP SWELLING

BACKGROUND OF THE INVENTION

1. Field of the Invention

The present invention relates in general to a method for detecting creep swelling in tubular members, and, in particular, to an ultrasonic method for detecting creep swelling in fossil utility steam lines and headers.

2. Description of the Related Art

The current method for detecting creep swelling in fossil utility steam lines and headers requires tedious mechanical measurements with a large caliper. The outside diameter of the pipe is measured rather than the circumference and so more than one measurement is required at a single location in order to check for out of roundness. As a result, the method is slow and the results are highly operator dependent. Additionally, the present method requires removal of insulation which can be very time consuming.

Other methods employed are based upon operational history and also plastic replication of material microstructure. Each technique has its own associated limitations and thus it is desirable to have several approaches to predict remaining lifetime.

The necessity for inspections is evidenced by reported steam line failures at power plants. The unanticipated failures of these components are potentially catastrophic to the plant operation as well as plant personnel and even may cause extensive damage to adjacent equipment.

Particular problems in inspecting arise when the pipes are composed in many short lengths with associated bends, wyes (y's), and tees (t's). This inaccessability problem is also increased with the presence of radiographic plugs, hangers and support systems.

Thus, there is a need for a rapid method for detecting creep swelling in fossil utility steam lines and headers. The method should require very little insulation removal and be suitable to scanning or acquiring close data points along the pipe or header in order to efficiently locate regions of creep swelling.

SUMMARY OF THE INVENTION

The present invention solves the aforementioned problems by providing an ultrasonic method for determining creep swelling in tubular members.

In accordance with the invention, ultrasonic surface waves are propagated around the pipe or the header in a circumferential direction. The transit time is measured and the circumferential dimension of the tubular member is determined therefrom. By comparing the measured dimension with the original dimension the diametrical change reflects a measure of the creep swelling in the tubular member. Based upon this measurement an estimate may be made as to the predicted "life" of the tubular member.

Accordingly, an aspect of the present invention is directed to a method for detecting creep swelling in fossil utility steam lines and headers which is rapid and measures circumference.

Another aspect of the present invention is to provide a method which scans or acquires close data points along a pipe or a header in order to efficiently locate regions of creep swelling.

Still another aspect of the present invention is to provide a method which only requires a small segment of the insulation from the piping to be removed which amounts in a significant cost reduction.

Still a further aspect of the present invention is to provide a method that is efficient and reproducible and may be used to make absolute measurements of diameter which serves as a baseline data bank.

The various features of novelty which characterize the invention are pointed out with particularity in the claims annexed to and forming a part of this disclosure. For a better understanding of the invention, and the operating advantages attained by its use, reference is made to the accompanying drawing and descriptive matter in which the preferred embodiment of the invention is illustrated.

BRIEF DESCRIPTION OF THE DRAWINGS

In the drawings:

FIG. 1 is a schematic representation of an arrangement for ultrasonically determining the creep swelling in a tubular member; and FIG. 2 is a representation of an oscillogram indicating the signals from successive transits of the pulse around the pipe.

DESCRIPTION OF THE PREFERRED EMBODIMENT

FIG. 1 schematically illustrates an arrangement for determining creep swelling in tubular members (10) such as a fossil utility steam line or header.

Often times the steam pipe is surrounded with an insulating material (12) depicted by the phantom line surrounding the steam pipe (10).

Advantageously, the method of the present invention requires only a small removal of the insulation (12) to provide an opening (14) in order to place the ultrasonic transducer (16) and wedge (18) in contact with the outer surface of the pipe (10). A small amount of commercial ultrasonic couplant, such as Ultragel II, a registered trademark of the General Electric company, is used between the wedge (18) and the metal surface of the pipe (10) in order to couple the sound into the metal.

Standard piezoelectric transducers (16) and plastic or ceramic wedges (18) are employed, for example those manufactured by Harisonic Laboratories. Alternatively, electromagnetic acoustic transducers (EMATs) are also suitable in the present invention for generating the ultrasonic waves. An advantage that EMATs have over conventional piezoelectric sensors is the fact that no ultrasonic couplant is required with EMATs. Accordingly, EMATs are ideal for applications involving continuous rapid scanning with data acquisition input to a computer.

The ultrasonic transducers (16) are connected to a pulser/receiver (20) by way of line or cable 22. A suitable pulser-receiver (20) includes Panametric's Model 5050 which due to its small size makes it very conducive to field inspection. The pulser-receiver (20) is then connected to an oscilloscope (24) by means of lines (26, 28). A computer system (30) may be connected to the oscilloscope (24) via line (32) to allow for continuous rapid scanning with data acquisition input.

Ultrasonic surface waves (34) are generated by means of the piezoelectric transducer (16) and wedge (18). The ultrasonic surface waves (34) are propagated around the pipe or header (10) in a circumferential direction as shown by arrow A in FIG. 1. The transit time of these ultrasonic surface waves is accurately measured by using the pulse overlap technique obtained from the $\Delta T$ readout as depicted in FIG. 2 in the oscilloscope (24). An oscilloscope (24) (such as the Tektronix 2236) allows this measurement to be made. This enables an accurate measurement of the absolute transit time. Alternatively, a field scope may be used, but an accurate standard is necessary for each size of pipe (10) examined. When there are a large number of different size pipes (10) involved, this is not practical. However, if only one size of pipe (10) is measured, then it is envisionable that a field scope is suitable. In the preferred embodiment an oscilloscope (24) is employed such as a Tektronix 2236 with ΔT capabilities. The use of the ΔT capability allows for the pulse-overlap method of measuring the time between successive transits. In this method, the pulses of two successive transits around the pipe (10) are precisely overlapped and the difference in time is read directly on the digital readout on the oscilloscope (24). This provides the most precise and accurate method of making a time measurement of this nature.

The ultrasonic surface waves (34) are generated with either a single wedge-transducer (18, 16) combination in a pulse-echo mode or two wedge-transducer (18, 16) combinations in a pitch-catch or transmit-receive mode.

The pulse-echo technique relies upon a multiple reflection at the contact point of the wedge (18) and the pipe (10) surface since the sound is actually propagating in the opposite direction to be directly received by the transducer-wedge combination (16, 18) after making a complete transit around the pipe (10). The signal amplitude obtained with the pulse-echo technique is not as large as the corresponding signal amplitude (with the same instrument setting) obtained with the pitch-catch technique. However, it is believed in all cases that the signal amplitude using the pulse-echo mode is more than adequate for pulse-overlap determination. The ultrasonic frequency range which offer the best results is 0.5 MHz to 1 MHz with the 0.5 MHz frequency end of the band being preferred. Higher frequencies tend to be attenuated by surface roughness over the long sound path necessary to make one or more transits around the pipe (10).

The circumferential dimension of the pipe (10) is obtained by multiplying the transit time ΔT by the known Raleigh velocity of sound in the material of the pipe (10).

This dimension is then compared with a reference dimension for the tubular member to calculate the percent diametrical change which then may be used to predict remaining useful life. The reference dimension normally is the original circumferential dimension of the pipe (10).

The method of the present invention was demonstrated on a calibration standard made from a section of electric resistance welded (ERW) tubing having an outer diameter (OD) of 10 inches with a wall thickness of ⅜ inch. This size represents an approximate lower size limit for hot reheat and main steam piping. Experience has shown that diametrical increases of 1% and 2% have been reported as being the criteria for determining serious creep damage. Consequently, the measured time interval for 1% changes in the diameter will be smallest for this size, and therefore, the least accurate. The calibration standard was turned on a lathe to provide for the relevant dimensions listed in Table 1.

TABLE 1

| Dimensions for the Calibration Standard | |
| --- | --- |
| Circumference of 0% Step | 33.750 |
| Circumference of 0.5% Step | 33.594 |
| Circumference of 1% Step | 33.406 |

The velocity of Raleigh waves used for the calibration is as follows:

$$V_{Raleigh} = 0.92 \, V_S$$
where $V_S$ = velocity of shear waves
 $= 1.271 \times 10^5$ in/sec
$V_{Raleigh} = 1.170 \times 10^5$ in/sec The derived changes in time T for the 1% and 0.15% steps were calculated by dividing the measured circumference by the Raleigh velocity for the 0%, 1% and 0.5% steps on the calibration standard. The derived transit times were then subtracted to give the predicted time shifts for the 0% and 1% steps. The results of the calculations are as follows:

$$\Delta T 1\% = 2.93 \, \mu sec$$
$$\Delta T 0.5\% = 1.35 \, \mu sec$$

The calculated time shifts were compared to the experimentally measured time shifts. The experimental error was a 7.85% for the pulse-echo mode and 2.33% for the pitch-catch mode for the 1% step. Since the 10 inch outer diameter pipe is approximately the smallest OD piping to be encountered in actual testing, this represents the worst case error. The 0.5% step presented problems due to apparent wavelength limitations caused from the small size of the tube.

When compared with the conventional methods for detecting creep swelling, the method of the present invention provides the following advantages. First, the only insulation that needs to be removed is a small segment large enough to place the wedge (18) in contact with the pipe (10) surface. Second, it is only necessary to place a sensor or transducer (16) in one position in order to determine creep swelling. In contrast, the conventional method requires a mechanical caliper to take measurements at several positions around the circumference. Third, the conventional mechanical caliper method is slow and the results are highly operator dependent. The method of the present invention is efficient and reproducible. Fourth, EMATs offer continuous scanning with data acquisition input into a computer (30).

Additionally, the present invention provides for making absolute measurements of diameter of tubular members (10) which would serve as a baseline "data bank" for comparison upon subsequent inspections.

The modifications to the procedure for absolute dimensional measurements are straightforward. In order to determine absolute dimensional measurements, it is necessary to subtract the time delay in the wedge from the "apparent" time for one complete transit around the pipe (10), or, in the case of pitch-catch measurements, the time delay in the wedge (18) and any slight misalignment of the entrance/exit points of the wedges (18) are also subtracted. This correction for either pulse-echo or pitch-catch techniques is accomplished by making a single laboratory measurement of the apparent transit time on a laboratory standard pipe of known dimension.

This "apparent" transit time is compared with the "true" transit time obtained by dividing the known circumference by the known Raleigh wave velocity. Subtracting the calculated transit time from the apparent time provides the correction that results from wedge delays and misalignments of pitch-catch wedges.

In practice then the correction is subtracted from transit time measurements made on actual steam piping (10). This corrected transit time multiplied by the Raleigh velocity yields the correct absolute circumference of the piping.

While a specific embodiment of the present invention has been shown and described in detail to illustrate the application of principles of the invention, certain modifications and improvements will occur to those skilled in the art upon reading the foregoing description. It is thus understood that all such modifications and improvements have been deleted herein for the sake of conciseness and readability but are properly in the scope of the following claims.

We claim:

1. A method for detecting creep swelling in a tubular member, comprising the steps of:

positioning at least one ultrasonic transducer on the tubular member;

propagating ultrasonic surface waves circumferentially around the tubular member with at least one ultrasonic transducer;

determining a transit time of the propagated waves around the tubular member by overlapping pulses of successive transits then measuring difference in time of same;

determining the circumferential dimension of the tubular member from the transit time and a known velocity of sound in similar material; and comparing the determined dimension with a reference dimension whereby a diametrical change in dimension reflects a measure of creep swelling in the tubular member.

2. A method as recited in claim 1, wherein the positioning step includes removing a sufficient amount of insulation for positioning the ultrasonic transducer.

3. A method as recited in claim 1, wherein the propagating step includes operating the at least one ultrasonic transducer at an ultrasonic frequency from 0.5 MHz to about 1.0 MHz.

4. A method as recited in claim 3, wherein the ultrasonic frequency is 0.5 MHz.

5. A method as recited in claim 1, wherein the positioning step includes two ultrasonic transducers operating in a pitch-catch mode.

6. A method as recited in claim 1, wherein the at least one ultrasonic transducer is at least one electromagnetic acoustic transducer.

* * * * *